United States Patent [19]
Gevins et al.

[11] Patent Number: 5,568,816
[45] Date of Patent: *Oct. 29, 1996

[54] EEG DEBLURRING METHOD AND SYSTEM FOR IMPROVED SPATIAL DETAIL

[75] Inventors: Alan S. Gevins, San Francisco; Jian Le, San Mateo, both of Calif.

[73] Assignee: Sam Technology, Inc., San Francisco, Calif.

[*] Notice: The term of this patent shall not extend beyond the expiration date of Pat. No. 5,331,970.

[21] Appl. No.: 276,700

[22] Filed: Jul. 18, 1994

Related U.S. Application Data

[63] Continuation-in-part of Ser. No. 868,724, Apr. 14, 1992, Pat. No. 5,331,970, which is a continuation-in-part of Ser. No. 578,880, Sep. 7, 1990, Pat. No. 5,119,816.

[51] Int. Cl.⁶ .............................................. A61B 5/0476
[52] U.S. Cl. ............................................................ 128/731
[58] Field of Search ...................................... 128/644, 731, 128/732; 364/413.05; 382/128

[56] References Cited

U.S. PATENT DOCUMENTS

| 4,416,288 | 11/1983 | Freeman | 128/731 |
|---|---|---|---|
| 4,736,751 | 4/1988 | Gevins et al. | 128/732 |
| 4,967,038 | 10/1990 | Gevins et al. | 128/644 |
| 5,038,782 | 8/1991 | Gevins et al. | 128/644 |
| 5,119,816 | 6/1992 | Gevins | 128/644 |
| 5,243,984 | 9/1993 | Ogura et al. | 128/731 X |
| 5,331,970 | 7/1994 | Gevins et al. | 128/731 |

*Primary Examiner*—Marvin M. Lateef
*Assistant Examiner*—Jeffrey R. Jastrzab
*Attorney, Agent, or Firm*—Eliot S. Gerber

[57] ABSTRACT

The spatial resolution of electroencephalograph (EEG) medical images is improved using "Deblurring" based on a digital computer based analysis using volumetric finite elements and a biophysical model of the passive electrical conductivity of a subject's head.

17 Claims, 3 Drawing Sheets

Deblurring Method and Software System

EEG DEBLURRING METHOD AND SYSTEM FOR IMPROVED SPATIAL DETAIL

This invention was made with government support under grants R43-NS32241, R44-NS27392, RO1-MH43324 awarded by the National Institutes of Health and the Alcohol, Drug Abuse, and Mental Health Administration. The Government has certain rights in the invention.

This application is a continuation-in-part application based in part on Application Ser. No. 07/868,724 for "EEG Spatial Enhancement Method & System", filed Apr. 14, 1992, now U.S. Pat. No. 5,331,970, issued Jul. 26, 1994, which is a continuation-in-part of 07/578,880 filed Sep. 7, 190 and is now U.S. Pat. No. 5,119,816.

BACKGROUND OF THE INVENTION

1. Field of the Invention

The invention relates to brain wave medical systems and methods and more particularly to an electroencephalograph (EEG) Deblurring system and method having improved spatial detail.

2. Description of Related Art

Electroencephalography is a simple noninvasive technique for monitoring brain function based on amplification of brain potentials recorded at the scalp. Although the EEG has been measured for over 65 years, its full potential as a technology for imaging brain function has not yet been realized. Its chief advantages when compared with other brain imaging technologies such as positron emission tomography or functional magnetic resonance imaging are: 1) millisecond-level temporal resolution necessary for resolving sub-second neurological processes; and 2) simplicity of the sensors (essentially a small piece of metal and an operational amplifier) which results in low cost and ability to record for prolonged periods of time in ordinary hospital rooms, at home, or even from ambulatory patients. The chief disadvantage of the traditional EEG method is poor spatial detail. There are two obstacles to substantially improving the detail of EEG recordings. The first is simply that more scalp recording sites are needed. While it is the usual clinical practice to record EEGs from 19 sites, it has been demonstrated with recordings from up to 124 sites that additional spatial information is readily available (Gevins et al, 1991, 1994). The U.S. Pat. No. 4,736,751, incorporated by reference, describes a system using a larger number of electrodes and various digital computer based methods to obtain more information from the brain wave signals. U.S. Pat. Nos. 4,967,038, 5,038,782, 5,119,816 and incorporated by reference, describe systems for conveniently obtaining EEG recordings from a larger number of electrodes and locating their positions.

The second obstacle is that spatial enhancement procedures are needed to reduce blur distortion that occurs as potentials generated in the brain are volume conducted through brain, cerebral spinal fluid, the low-conductivity skull, and scalp to the recording electrodes at the scalp surface. Spatial enhancement is possible since the 3 dB point of the point spread function for conductance of potentials from the brain surface to the scalp averages about 2.5 cm; with 128 electrodes spaced evenly on an average adult head, the interelectrode distance is about 2.25 cm. U.S. patent application Ser. No. 07/868,724 for "EEG Spatial Enhancement Method & System", filed Apr. 14, 1992, now U.S. Pat. No. 5,331,970, issued Jul. 26, 1994 and incorporated herein by reference, describes a system and method, called Deblurring, which improves the spatial detail of the EEG based on measurements of the positions of the electrodes on the subject's head, measurements of the subject's head size, shape, scalp thickness, skull thickness and brain shape, and estimates of the conductivity of the skull, scalp and cerebral spinal fluid. However, the method requires a means of measuring each electrode position, a Magnetic Resonance Image or other means of measuring the subject's head size, shape, scalp thickness, skull thickness and brain shape, a considerable amount of manual effort in order to trace out structures from a subject's Magnetic Resonance Image, as well as a large amount of computation time.

OBJECTIVES AND FEATURES OF THE INVENTION

It is an objective of the current invention to reduce the amount of manual effort required to improve the spatial detail of scalp EEG images. It is a further objective of the current invention to reduce the amount of computation required to improve the spatial detail of scalp EEG images. It is a further objective of the current invention to eliminate the requirement of a Magnetic Resonance Image or other device for measuring the internal structure of the head in order to improve the spatial detail of scalp EEG images. It is a feature of the current invention to automate the generation of finite element models of a head which are used to improve the spatial detail of scalp EEG images. It is another feature of the current invention to reduce the amount of computing time required to improve the spatial detail of scalp EEG images by replacing the iterative method of computing deblurred scalp EEG images with a more efficient direct numerical method.

SUMMARY OF THE INVENTION

In accordance with the present invention, there is provided a method and system, called Debluro ring, to improve the spatial resolution of electroencephalograph (EEG) medical images using a realistic finite element biophysical model of the passive conducting properties of each subject's head to estimate a potential distribution at the cortical surface. The volumetric finite elements are automatically generated by a digital computer using anatomical information obtained with, or without, Magnetic Resonance Images or other devices for measuring the internal structure of the head. The finite elements are constructed in such a way that the transformation matrix relating a potential distribution at the scalp to a potential distribution on the brain surface is invertible, allowing a direct computation of the cortical potential distribution and achieving a computational speedup of approximately 10,000 over prior iterative methods.

BRIEF DESCRIPTION OF THE DRAWINGS

Other objectives and features of the present invention will be apparent from the following detailed description, taken in conjunction with the accompanying drawings. In the drawings:

FIG. 3A shows an initial ray tracing with circles at brain, skull and scalp surfaces. FIG. 3B shows a number of rays and the constructed finite elements.

FIG. 4A shows scalp EEG data recorded during stimulation of the middle finger of the left hand. FIG. 4B shows the same data after application of the Deblurring method.

DETAILED DESCRIPTION OF THE INVENTION

Figure 1:
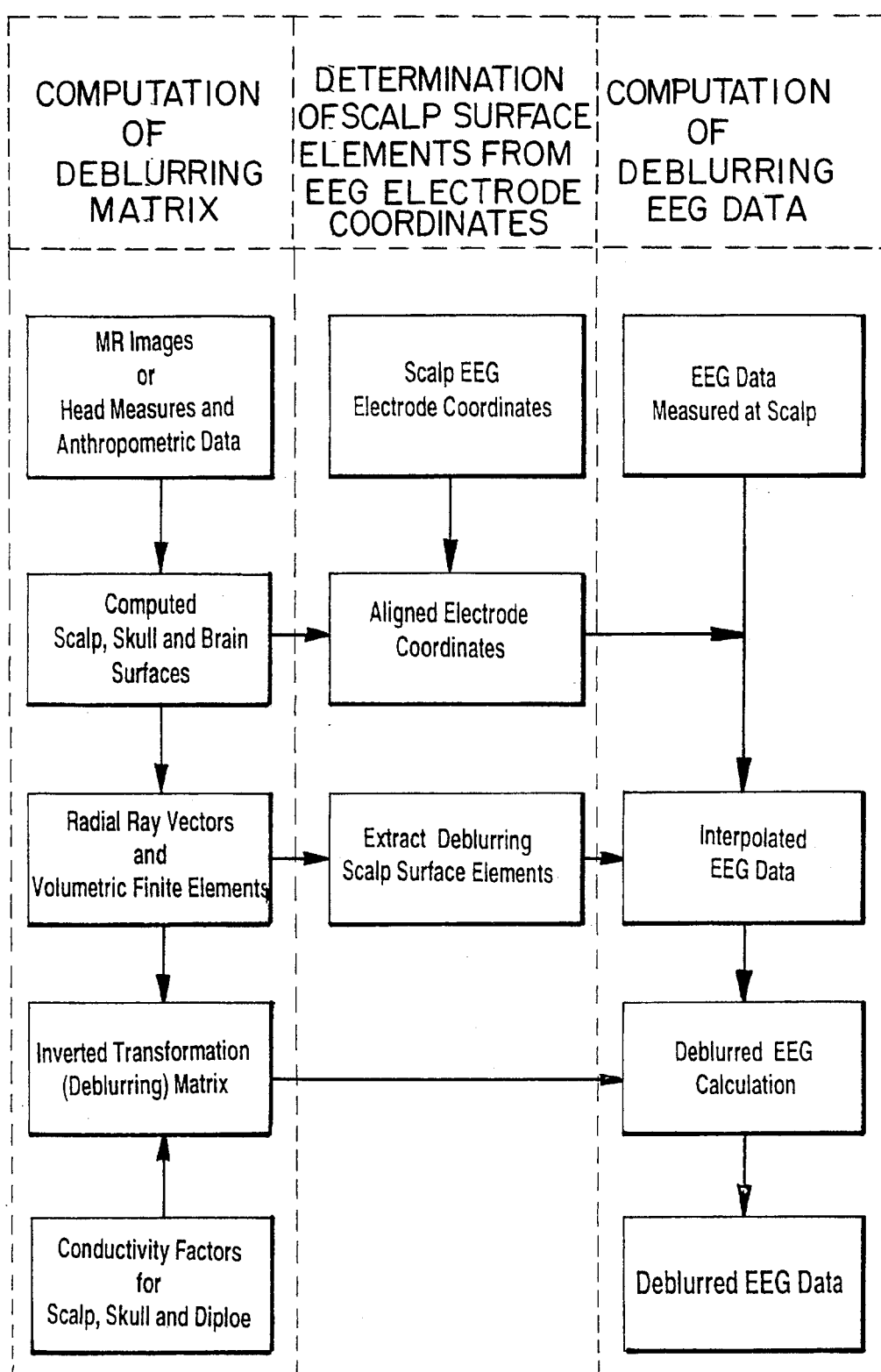
FIG. 1 is a schematic block diagram of the system of the current invention.

The present invention is illustrated in FIG. 1. As shown therein, there are three main processes, represented in three vertical columns of subprocess boxes. The processes are: 1) Computation of Deblurring Matrix; 2) Determination of Scalp Surface Elements from EEG Electrode Coordinates; and 3) Computation of Deblurred EEG Data. The left column shows how the inverted finite element transformation matrix (Deblurring Matrix) is computed from data about head shape and size and tissue thicknesses. These data are obtained from MR images or from direct head measurements and anthropometric data and are used to automatically compute scalp, skull and outer brain surfaces. Imaginary mathematical radial ray vectors are radially projected through the computed scalp, skull and outer brain surfaces and prism shaped finite elements are made from triangles on two adjacent surfaces whose edges are defined by connecting points of intersection (mesh points) of the ray vectors with the three surfaces. Conductivity factors for scalp, skull, and diploe (porous bone layer) are obtained by estimation as described in U.S. patent application Ser. No. 07/868,724, now U.S. Pat. No. 5,331,970, or by reference to anthropometric data as described herein. These conductivity values are then used, in a software program run on a digital computer, to determine the actual conductivity of each finite element, and a transformation matrix relating the potential distribution at the brain (cortical) surface with the potential distribution at the scalp is computed using Poisson's equation. This transformation matrix is inverted, an operation made possible by the manner of constructing volumetric finite elements from mesh points defined by radial ray vectors. The middle column shows how the boundaries of the scalp surface elements are determined from the EEG electrode coordinates. First, EEG electrode coordinates are determined by direct measurement or estimation as described in U.S. Pat. No. 5,119,816. These coordinates are then aligned with the computed scalp surface using fiducial reference points and mathematical surface alignment algorithms as described in U.S. Pats. No. 4,736,751 and 5,119,816. The boundaries of the scalp surface elements are then determined by a common area of patches determined by the aligned scalp electrode coordinates and the scalp mesh points defined by the radial ray vectors. The fight column shows how the Deblurred EEG data are computed from the EEG data measured at the scalp. First the scalp-recorded EEG is interpolated to make a potential distribution which can be associated with each of the scalp surface elements (the finite element vertices at the scalp surface) as determined from process 2). Then the Deblurred EEG data are computed by multiplying the interpolated EEG data by the Inverted Transformation Matrix determined in process 1).

1. More Automated Finite Element Modeling of Scalp and Skull Layers with MRIs

1.1 Deriving the tissue delineating surfaces

The air/scalp, scalp/skull, and skull/cortex tissue boundaries are found automatically using a software program for boundary surface detection, in a digital computer, by exploiting the facts that these surfaces are relatively large and are characterized by significant image contrast in T1-weighted MRIs. The MRI image data is preferably entered into the digital computer memory using a tape drive or a black-white scanner. The first-order and second-order partial derivatives of the 3-D image intensity function, $E(x, y, z)$, are estimated at multiple spatial resolutions (scales), using 3-D filter kernels derived from the uniform tricubic B-spline basis function. At each scale, candidate surfaces of interest are automatically constructed that pass through local extrema of the magnitude of the 3-D image intensity gradient, $|\nabla E|$.

Figure 2:
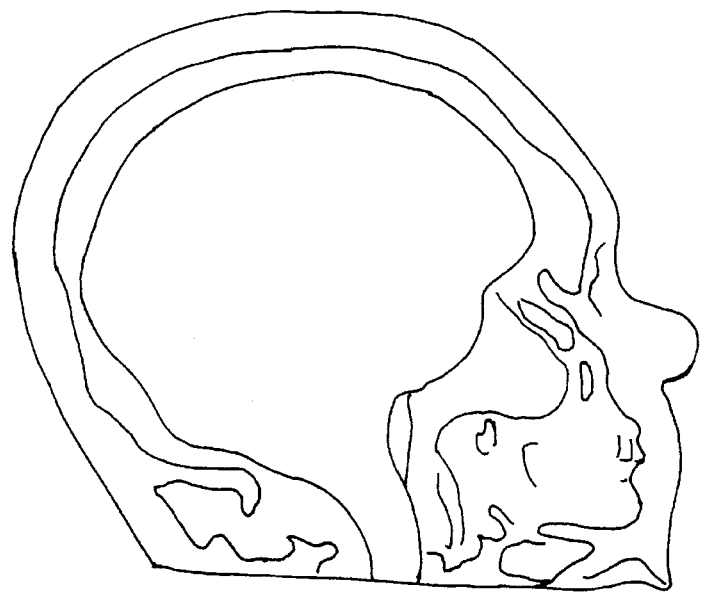
FIG. 2 shows the automatic construction of the scalp, skull and brain surfaces from a subject's MRIs.

The candidate surfaces are sorted first by the number of points that they contain, then by the average image intensity gradient magnitude $|\nabla\nabla E|$ across the surfaces, and last by the spatial extents of the boxes that bound the surfaces. Typically this automatically identifies the three surfaces of interest, which delineate the scalp and skull layers. FIG. 2 shows an example of this process. The accuracy of the automatic surface identification is checked by confirming that the skull/cortex surface is contained completely within the scalp/skull surface, which in turn is contained completely within the air/scalp surface. Also, it is verified that the gradient vector $\nabla E$ is directed generally inward (toward the centroid of the surface) across the air/scalp and skull/cortex surfaces, and directed generally outward (away from the centroid of the surface) across the scalp/skull surface.

1.2 Constructing the finite element model

Figure 3A:
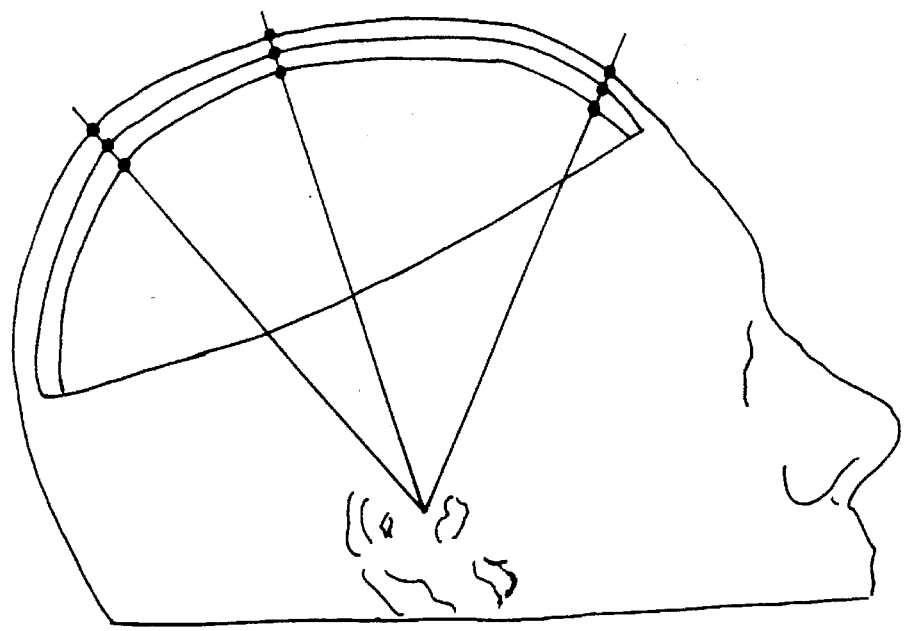
FIGS. 3A and 3B show the construction of finite elements.
Figure 3B:
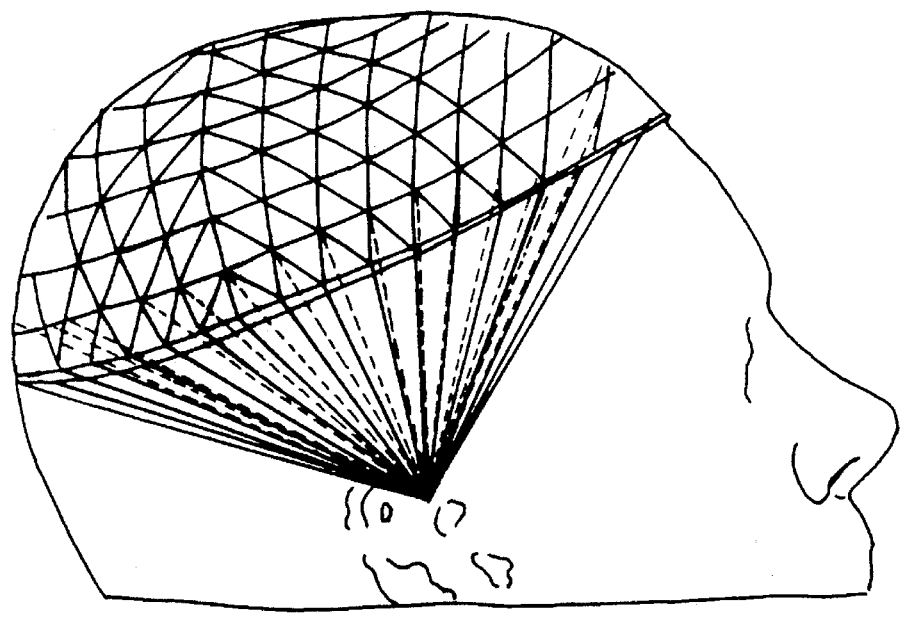

Finite element mesh points are derived when a chosen set of regulating ray vectors is radially projected through the computed scalp, skull, and outer brain surfaces. The mesh points on the scalp, skull and outer brain surfaces are triangularized, and prism-shaped finite elements are formed from two triangles located on adjacent surfaces. FIG. 3 illustrates this process.

1.3 Choosing a set of regulating ray vectors

The accuracy of the deblurred data is affected by the spatial distance between finite element mesh points and the spatial relations among finite element vertices within each finite element. The choice of the regulating set of ray vectors used to construct the finite element model "regulates" these factors. The choice of number of ray vectors determines the spatial distance between mesh points, and choice of the configuration of these ray vectors determines the condition number of the forward solution matrix which, in turn, determines the stability of the explicitly-inverted finite element transformation matrix used in subsequent deblurring operations. We have found that a set of unit length vectors, which are the vertices of a group of triangles whose sides have nearly equal length, is an optimal solution.

2. Finite Element Modeling of Scalp and Skull Layers without MRIs

2.1 Constructing a subject-specific head model from tape measurements and a subject's physical attributes Information regarding an individual subject's head shape and size, body weight, sex and age along with anthropometric statistics on scalp and skull thicknesses and conductivities are used to construct a subject-specific head model when MRI data is not available.

The subject's actual head shape can be derived either from direct measurement with a three dimensional digitizer as described in U.S. Pat. No. 5,119,816, from automatic or manual measurement of several standard cross-directional lines and classification according to predetermined head shape classes as described in U.S. Pat. No. 5,119,816. These data are interpolated as needed and are used to construct a scalp surface model. In the simplest case, the nasion to inion distance, the distance between preauricular notches and the circumference of the head are measured with a tape measure, classified according to predetermined head shape class and a rough approximated scalp surface model is computed. The subject's physical attributes such as height, weight, age, sex and race are then used to approximate the scalp and skull layer thicknesses at different spatial locations on the head using thickness formulae described in the literature (Pensler and McCarthy, 1985; Adeloye et al, 1975). A non-linear parametric estimation technique is employed to improve the reported formulae using measured skull and scalp thicknesses from MRIs derived from a diverse group population of subjects.

2.2 Constructing the finite element model

Choosing a set of regulating ray vectors is the same as described in Section 1.3. Finite element mesh points at the scalp are derived by radially projecting a chosen set of regulating ray vectors through the scalp surface model obtained from head measurements. Then skull and outer brain mesh points are determined by moving the scalp mesh points radially inward along each ray vector by the appropriate local scalp and skull thickness derived from the tissue thickness formulae. The mesh points on the scalp, skull and outer brain surfaces are triangularized, and prism-shaped finite elements are formed from two triangles located on adjacent surfaces.

3. FEM Deblurring Calculations

The Deblurring algorithm uses the Finite Element Method (FEM) to discretize Poisson's equation which is used to solve the bioelectric volume conduction problem. A fundamental formula is derived from the Finite Element Method which yields the numerical forward solution of the potential distribution at the scalp by multiplying a FEM-based transfomation matrix (embodying a model of the conducting tissues) by the conical (outer brain) potential distribution. Since the conical potential distribution is unknown and since the controlling information is measured at the scalp, this formula has to be iterated using an optimization scheme until a suitable set of conical data is found whose forward solution best fits the measured scalp data as described in U.S. patent application Ser. No. 07/868,724, now U.S. Pat. No. 5,331,970.

However, the volumetric finite elements (three-dimensional volumes) representing the conducting tissues can be generated in a manner such that the corresponding FEM-based transformation matrix is invertible. Therefore the desired cortical data can be derived by directly multiplying the inverted transformation matrix by the measured scalp data. The FEM modeling strategies described in Sections 1 and 2 were designed and developed to accommodate this direct approach to extract the desired cortical data.

The improved Deblurring procedure was developed based on the notion that the resulting deblurring region, $\Omega$, obtained with strategies outlined in Sections 1 and 2 has a total of 3*n FEM mesh points where each tissue delineating surface has n FEM mesh points. The boundary of the region $\Omega$ is bordered by the scalp surface and the outer brain surface extending from the top of the head to a cut-off surface determined by the intersection points of the edge vectors of the chosen set of regulating ray vectors with the three tissue delineating surfaces. If the designated outer brain surface has rn FEM edge points, the boundary surface of this deblurring region $\Omega$ will have a total of 2*n+m FEM mesh points with n points on the scalp surface, n points on outer brain surface and m points on the edges of the scalp/skull border. With this FEM montage, Poisson's equation is discretized and the fundamental numerical formula is established as follows:

$$u_1 = A u_3 \tag{1}$$

where $u_1$ represents the n potential values at the scalp surface, $u_3$ represents the n+m potential values at the outer brain and the cut-off surfaces. The resulting matrix A is the FEM-based transformation matrix that has a dimension of n×(n+m). A detailed discussion on how to derive Eq.(1) can be found in U.S. patent application 07/868,724, now U.S. Pat. No. 5,331,970. To warrant a unique solution, the existing deblurring region $\Omega$ is modified slightly when the physical locations of the FEM outer brain edge points are clamped to the scalp/skull edge points such that the total number of FEM points on the boundary surface of the modified deblurring region becomes 2*n and the corresponding numerical formula becomes:

$$u_1 = \hat{A} \hat{u}_3$$

where $\hat{A}$ is a square and invertible matrix.

Figure 4A:
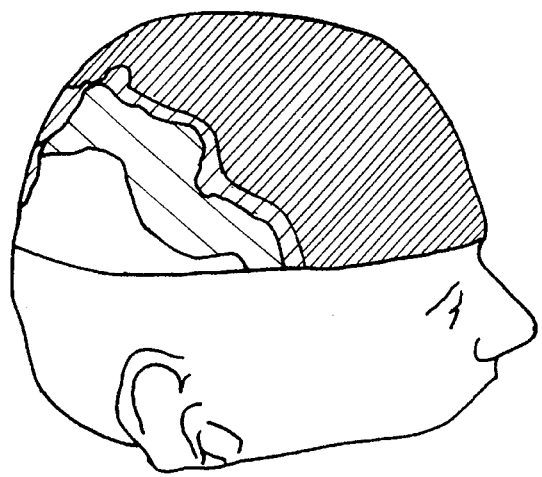
FIGS. 4A and 4B show an example of application of the improved Deblurring method.
Figure 4B:
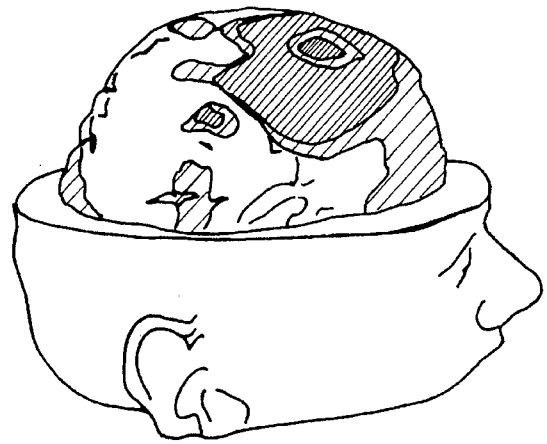

With this direct matrix inversion approach, the computational performance of the Deblurring method has been improved by a factor of about 10,000. FIGS. 4A and 4B show an example of application of the improved Deblurring method. FIG. 4A shows scalp EEG data recorded during stimulation of a middle finger of the left hand. FIG. 4B shows the same data after application of the Deblurring method.

4. Modeling the Diploe Layer of the Skull

The above implementation uses a two layered finite element model which represents the scalp and skull as homogeneous tissues. Though good results have been reported with this modeling strategy (Gevins et al. 1994), we have found that further improvement can be made by modeling the skull as a three-layered, sandwich-like structure consisting of two different tissue types: the inner and outer tables (layers) of resistive compact bone separated by a highly conductive porous bone layer called the diploe. A numerical simulation study (which utilized finite element models that represented the skull as either a homogeneous or an inhomogeneous tissue) has shown that improperly modeling the skull as a homogeneous tissue can overestimate the cortical potential magnitudes by 25 to 37 percent though the spatial pattern generally remains unchanged. Although two more tissue delineating surfaces (outer-table/diploe and dipole/inner-table) can be introduced for the MRI-based and MRI-less FEM modeling strategies, it has been reported by Law (1993) that the outer table and inner table have a uniform thickness for most subjects. Therefore intersection points of the chosen ray vector with the outer-table/diploe and diploe/inner-table surfaces are found by moving the scalp/skull and skull/outer brain intersection points by a fixed amount along the given ray vector. To warrant a unique solution, the physical locations of the FEM outer brain edge points will still be clamped to the scalp/skull edge points such that the resulting matrix Â is still square and invertible.

REFERENCES

Adeloye, A., Kattan, K. R. and Silverman, F. N. (1975) Thickness of the normal skull in American blacks and whites. Am. J. Phys. Anthrop., 43: 23–30.

Gevins, A. S., Le, J., Brickett, P., Reutter, B. and Desmond, J. (1991) Seeing through the skull: advanced EEGs use MRIs to accurately measure cortical activity from the scalp. Brain Topography, 4(2), Human Sciences Press, Inc.: New York, pp. 125–131.

Gevins, A. S., Le, J., Martin, N., Brickett, P., Desmond, J. and Reutter, B. (1994) High resolution EEG: 124-channel recording, spatial deblurring and MRI integration methods. Electroenceph. clin. Neurophysiol., 90: 337–358. Law, S. K. (1993) Thickness and Resistivity Variations over the Upper Surface of the Human Head. Brain Topography, 6: 99–109. Le, J. and Gevins, A. S. (1993) Method to reduce blur distortion from EEG's using a realistic head model. IEEE Trans. Biomed. Eng., 40: 517–528. Pensler, J. and McCarthy J. G. (1985) The Calvarial Donor Site: An anatomic study in cadavers. Plastic and. Reconstructive Surgery, 75: 648–651.

What is claimed is:

1. A method of improving the resolution of data recorded from a plurality of electroencephalograph (EEG) electrodes removably and electrically connected to the scalp of a subject including the steps of:
   (a) amplifying brain waves detected at the electrodes, converting the amplified brain waves into digital data and entering the data into a computer system means to analyze the data;
   (b) in the computer system means forming a finite element transformation matrix based upon an imaginary division of the subject's head into three dimensional finite elements, the matrix being calculated based upon data regarding the subject's head shape, size and tissue thicknesses;
   (c) determining the conductivity of each finite element based upon the thickness of each finite element and conductivity values for relevant portions of a head;
   (d) measuring physical locations of the electrodes on the subject; and
   (e) entering the electrode locations measured in (d) and conductivities determined from (c) into the computer system means to analyze the recorded brain wave data and to provide a computation of outer brain surface electrical potential distribution.

2. The method as in claim 1 and including the steps of forming the finite elements by imaginary mathematical unit length ray vectors radially projected through the subject's head tissue boundaries to form prism-shaped finite elements.

3. The method as in claim 2 and including the step of forming the prism-shaped finite elements from triangles whose sides have nearly equal length on two adjacent surfaces whose edges are defined by connecting points of intersection of the ray vectors with at least three adjacent tissue delineating surfaces including outer brain surface, skull and scalp, derived from brain imaging including MRI.

4. The method as in claim 2 wherein including the step of placing a scalp mesh defined by the radial ray vectors in the vicinity of each scalp electrode.

5. The method as in claim 1 wherein determining conductivity values include determiing conductivity values for scalp, skull and diploe.

6. The method as in claim 5 and including the step of determining the conductivity values by reference to anthropometric data.

7. he method as in claim 1 and performing the analysis of (e) using a transformation matrix relating potential distribution at outer brain surface with potential distribution at scalp surface using Poisson's equation.

8. A method as in claim 7 and including the step of inverting the transformation matrix to provide an inverted transformation matrix.

9. A method as in claim 8 and including the step of interpolating an EEG recording from the subject at each scalp surface to provide a potential distribution and multiplying the interpolated EEG data by the inverted transformation matrix.

10. The method of claim 1 and including the step of analyzing the subject's head in (b) as having a total of K*n mesh points where each of K tissue delineating surfaces has n mesh points.

11. The method as in claim 10 and including the step of establishing a relationship between a number representing edges of a set of regulating ray vectors intersected with tissue delineating surfaces to a number representing mesh points, where in case of three surfaces, outer brain surface has m edge points, boundary surface of this region has a total of 2*n+m mesh points with n points on scalp surface, n points on outer brain surface, and m points on edges of the scalp/skull border.

12. The method as in claim 11 and including the step of deriving in claim 1(b) the transformation matrix using a Finite Element Method (FEM) based transformation matrix.

13. The method as in claim 12 and including the step of and using the Finite Element Method (FEM) to create FEM-based transformation matrices which mathematically model conducting tissues between the scalp and outer brain surfaces.

14. The method as in claim 12 and including the step of obtaining a numerical forward solution of the potential distribution at the scalp by multiplying the FEM-based transformation matrix by an outer brain potential distribution.

15. The method as in claim 12 and including the step of inverting the FEM-based transformation matrix to provide an inverted transformation matrix.

16. The method of claim 15 and including the step of deriving outer brain surface data by multiplying the inverted transformation matrix by measured scalp data.

17. The method of claim 1 and including the step of using an algorithm using the Finite Element Method (FEM) to discretize Poisson's equaltion to solve a bioelectric volume conduction problem.

* * * * *